United States Patent [19]

Waters

[11] 3,997,404
[45] Dec. 14, 1976

[54] METHOD AND APPARATUS FOR CHARACTERIZING BIOLOGICALLY ACTIVE AGENTS

[75] Inventor: John R. Waters, Towson, Md.

[73] Assignee: Johnston Laboratories, Inc., Cockeysville, Md.

[22] Filed: May 27, 1975

[21] Appl. No.: 581,277

Related U.S. Application Data

[63] Continuation-in-part of Ser. No. 477,452, June 7, 1974, Pat. No. 3,944,471.

[52] U.S. Cl. .......................... 195/103.5 R; 195/127; 195/139
[51] Int. Cl.[2] .......................................... C12K 1/04
[58] Field of Search ............. 195/103.5 R, 127, 139

[56] References Cited
UNITED STATES PATENTS

| | | | |
|---|---|---|---|
| 2,914,447 | 11/1959 | Levin | 195/103.5 R |
| 3,506,402 | 4/1970 | Simon | 195/103.5 R |
| 3,676,679 | 7/1972 | Waters | 195/127 |
| 3,819,489 | 6/1974 | Kronick et al. | 195/103.5 R |
| 3,844,894 | 10/1974 | Kronick et al. | 195/103.5 R |

*Primary Examiner*—A. Louis Monacell
*Assistant Examiner*—Robert J. Warden
*Attorney, Agent, or Firm*—Schuyler, Birch, Swindler, McKie & Beckett

[57] ABSTRACT

A method for characterization of biological activity comprising providing a plurality of gas-tight cells each having a light-permeable wall section, each cell containing a different $^{14}C$-labeled fermentable substrate, a carbon dioxide absorber and a scintillation compound in intimate proximity to each other remote from said substrate, and an axenic sample of a biologically active material; subjecting said cells to conditions conducive to biological activity and thereafter measuring the light emitted by the scintillation compound as a result of the decay of $^{14}CO_2$ generated by the metabolic action of the biologically active agent in said sample on said substrate and captured by the carbon dioxide absorber. Apparatus is provided comprising a plurality of sterile chambers containing different $^{14}C$-labeled fermentable substrates, means to facilitate introduction of an axenic sample of a biologically active agent into each chamber, means for sealing each chamber to form a gas-tight cell having a light-permeable wall section, and a carbon dioxide absorber and a scintillation compound in intimate proximity to each other in each cell adjacent the light-permeable wall section.

47 Claims, 6 Drawing Figures

METHOD AND APPARATUS FOR CHARACTERIZING BIOLOGICALLY ACTIVE AGENTS

This application is a continuation-in-part of my co-pending patent application Ser. No. 477,452 filed June 7, 1974, the entire disclosure of which is expressly incorporated herein by reference.

BACKGROUND OF THE INVENTION

This invention relates to a method and apparatus for characterizing biological activity. More particularly, this invention relates to a rapid an economical method and apparatus for identifying microorganisms, viruses, enzymes, etc. through an analysis of their activity toward fermentation of common biodegradable substances. The term "fermentable" is intended to mean capable of being broken down into simpler compounds by the action of a biologically active agent. The invention is especially suitable for identifying medically significant bacteria by monitoring the light produced by a scintillation compound as a result of the generation of $^{14}CO_2$ by the action of the bacteria on various $^{14}C$-labeled carbohydrates, amino acids, alcohols, acid salts, etc.

While the invention might most commonly be utilized for the identification of medically significant bacteria, it has utility in the characterization of algae, protozoa, fungi, yeasts and viruses, and even may find potential application in the characterization of active enzymes.

The ability to identify a biologically active agent is of obvious importance, in medicine, in pharmaceutical testing, in the food processing industry, in research applications, and in many other fields. Prior art procedures for identifying bacteria involve long, drawn out and tedious sequences of culturing and complex observations. Results are generally not available for 24 to 48 hours or longer, and even then are fraught with uncertainty due to the subjective nature of observations which must be made by individual technicians.

Methods have been proposed for the detection of biological activity by measuring the $^{14}CO_2$ produced by fermentation of $^{14}C$-labeled fermentable substances; see Walters, U.S. Pat. No. 3,676,679; Wagner, *Principles of Nuclear Medicine*, pp. 796–7, published by W. B. Saunders, Philadelphia, 1968. However, the thrust of such prior efforts has been toward simple detection of the presence or absence of any biologically active species in the system. Once biological activity was found, it was still necessary to resort to the old culturing and observation procedures in order to identify the biologically active agent.

It has been known for some time that not all fermentable substrates are broken down into simpler compounds by all biologically active agents. In other words, biologically active agents show a certain selectivity in the substrates which they will ferment. This gives rise to a pattern of activity or "fingerprint" which is characteristic for each species of biologically active agent and which thus may be useful in identifying particular biologically active agents.

The fingerprint or activity pattern of a given biologically active species may be related to standard classification schemes by the use of standard common known organisms.

As used herein, the term "biologically active agent" is intended to refer to various types of microorganisms and related substances including fungi, protozoa, algae, yeasts, bacteria, viruses, enzymes, etc.

It is an object of the present invention to provide a method and apparatus for characterizing biologically active agents.

More particularly, it is an object of the invention to provide a method and apparatus for identifying biologically active agents by determining a characteristic fermentation activity pattern or fingerprint for such agents.

It is a further object of the invention to provide a method and apparatus capable of providing objective data on a biologically active agent without the necessity of subjective observations by a laboratory technician.

It is an object of the invention to develop a simple, preformed assembly for characterizing a biologically active agent which requires little operator handling.

It is another object of the invention to provide a simple inexpensive apparatus which may be economically discarded after a single use.

It is yet another object of the invention to provide a method and apparatus for characterizing a biologically active agent which can be readily automated.

It is also an object of the invention to provide a method and apparatus in which incubation of the test sample and subsequent analysis thereof take place in the same chamber.

It is also an object of the invention to provide a method and apparatus for characterizing biological activity which can provide useful information much more rapidly than prior art methods.

Further objects of the invention will appear from a consideration of the following specification.

SUMMARY OF THE INVENTION

These and other objects of the invention are achieved by providing a method for characterization of biological activity comprising the steps of:

providing a plurality of gas-tight cells each having a light-permeable wall section, each cell containing (1) a different $^{14}C$-labeled fermentable substrate, (2) a carbon dioxide absorber and a scintillation compound in intimate proximity to each other adjacent the light-permeable wall section remote from the $^{14}C$-labeled fermentable substrate; and (3) an axenic sample of a biologically active agent;

subjecting said cells to conditions conducive to biological activity for a pre-determined period of time; and thereafter measuring the light emitted by said scintillation compound in each cell through said light-permeable wall section.

In one preferred embodiment of the method of the invention, the gas-tight cells are provided by: providing a plurality of sterile chambers each containing a different $^{14}C$-labeled fermentable substrate; introducing an axenic sample of a biologically active agent into each chamber; and sealing the chambers with a gas-tight transparent cover having a carbon dioxide absorber and a scintillation compound coated on the inside thereof in intimate proximity to each other.

The objects of the invention are also achieved by providing apparatus for the identification of biologically active agents comprising:

a plurality of sterile chambers each containing a different $^{14}C$-labeled fermentable substrate, means to facilitate introduction of an axenic sample of a biologically active material into each chamber, means for sealing each chamber to form a gas-tight cell having a light-permeable wall section, a carbon dioxide absorber in each chamber, and a scintillation compound in each chamber in intimate proximity to said carbon dioxide absorber; the carbon dioxide absorber and scintillation compound in each cell being disposed adjacent the light-permeable wall section thereof and remote from the $^{14}$C-labeled fermentable substrate.

BRIEF DESCRIPTION OF THE DRAWINGS

The invention will be further explained with reference to the accompanying drawings wherein.

DETAILED DESCRIPTION OF THE PREFERRED EMBODIMENTS

Figure 1:
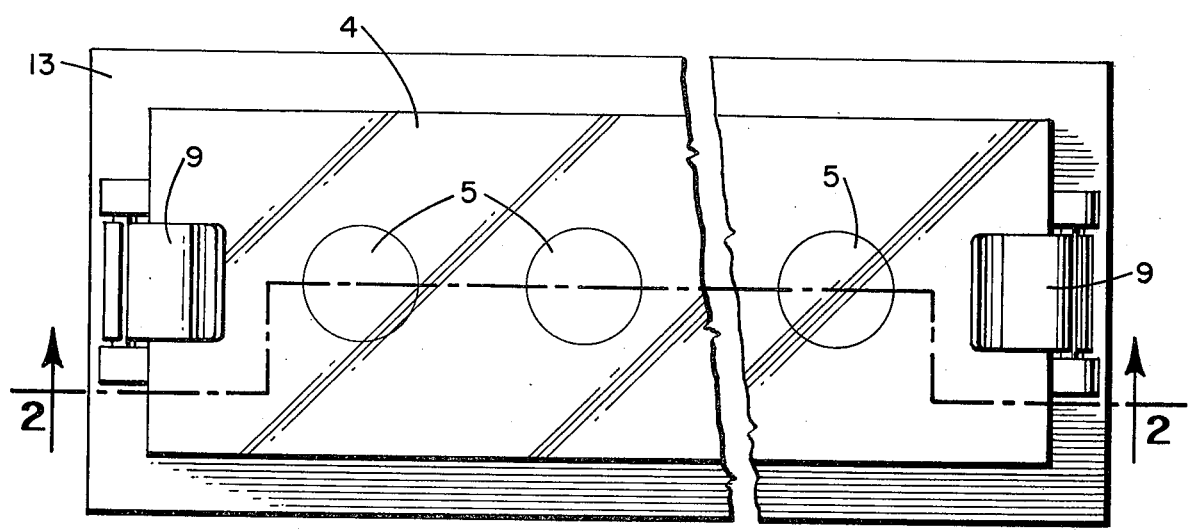
FIG. 1 is a plan view of a preferred form of apparatus according to the instant invention.
Figure 2:
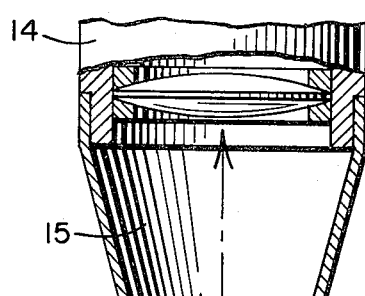
FIG. 2 is a sectional view taken along line 2—2 of FIG. 1.
Figure 3:
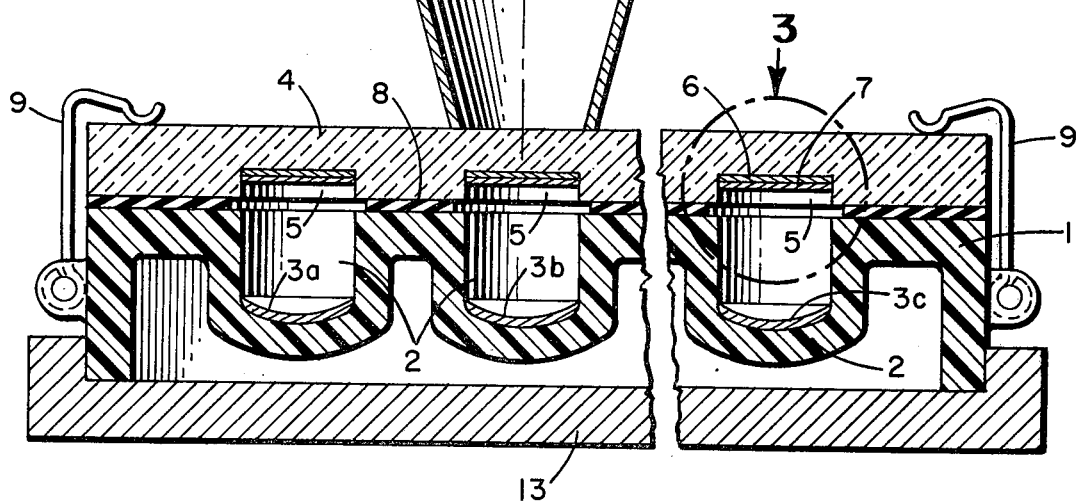
FIG. 3 is an enlarged sectional view of the encircled portion of FIG. 2.
Figure 3:
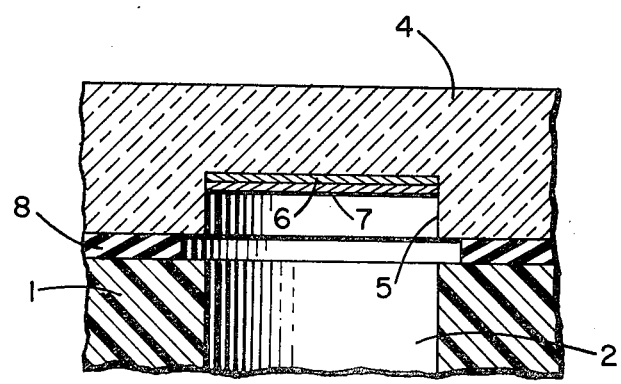

The preferred embodiment of the apparatus of the invention comprises a tray 1 formed with a linear array of chambers 2. Tray 1 must be made of a sterilizable material. A rigid, opaque plastic such as acrylonitrile-butadiene-styrene, polystyrene, polypropylene, polyvinylchloride, etc. would be suitable. A typical size for the tray might be ¾ on an inch wide by 8 inches long with each chamber being a cylindrical recess ¼ deep and ¼ inch in diameter. The number of cells can also vary depending on the requirements of the identification to be undertaken. Since ordinarily a test of up to twenty substrates will provide an adequate activity fingerprint to characterize most microorganisms, each tray might suitably be provided with twenty chambers.

In the bottom of each chamber 2 is a different metabolizable substrate material 3a, 3b, 3c, etc. For example, substrate 3a might be a carbohydrate such as glucose; substrate 3b might be an amino acid such as phenylalanine, and substrate 3c might be an organic acid such as citric acid.

In general the different substrates may be selected from among the class of microbiologically metabolizable carbon compounds including carbohydrates, amino acids, carboxylic acids, amines, polyhydroxy alcohols, hydroxy acids, etc.

| | | |
|---|---|---|
| fructose | lysine | aspartate |
| maltose | glycine | fumarate |
| sucrose | alanine | glutamate |
| glucose | xanthine | succinate |
| xylose | tyrosine | malonate |
| galactose | threonine | pectate |
| mannose | histidine | alginate |
| lactose | leucine | acitate |
| arabinose | serine | tartrate |
| raffinose | valine | tryptophan |
| rhamnose | arginine | uracil |
| dulcitol | phenylalanine | starch |
| sorbitol | ornithine | cellulose |
| mannitol | urea | salicin |
| erythritol | citrate | propionate |
| adonitol | lactate | butyrate |
| inositol | formate | inulin |
| glycerol | oxalate | trehalose |

Each metabolizable substrate is labeled with a radioactive isotope of carbon having an atomic weight of 14 (hereinafter referred to as $^{14}$C). The substrate compounds may be fully substituted, i.e. every carbon atom of the substrate molecules is a $^{14}$C atom. However, it is recognized that labeled substrates in which one or more carbon atoms at reactive sites in the molecule are $^{14}$C atoms, would be useful in the invention.

For maximum sensitivity, all of the carbon atoms in the $^{14}$C-labeled substrate are preferably replaced by $^{14}$C atoms, although this is not absolutely necessary so long as the $^{14}$C is substituted in the correct position in the substrate molecules so that it is liberated as $^{14}CO_2$. In this regard, it should be noted, as is well understood by those skilled in the art, that the $^{14}$C cannot be substituted at random in the substrate molecules, but its position must be carefully selected.

The preferred technique for depositing the substrate materials in the chambers is to pipette a known volume of a solution of the substrate having a known concentration into the chamber, and then to evaporate the solvent. This leaves a coating of the substrate material on the bottom of each chamber.

Alternatively, the $^{14}$C-labeled substrates could be incorporated in molten agar which thereafter could be deposited in each chamber and allowed to cool and solidify. A further possibility would be to absorb a solution of the $^{14}$C-labeled substrate on a small disc of sterile absorbing paper (e.g. filter paper) which could be dried and then dropped into each chamber just before use.

Large quantities of substrate are not required. As little as $10^{-8}$ moles or $10^{-6}$ grams with a $^{14}$C activity of 0.1 microcuries or less will ordinarily suffice. The amount of $^{14}$C-labeled substrate in each cell is determined by the sensitivity of the light detection system and the permissible duration of the fermentation process. The total activity in each cell can be in the range from 0.01 to 5 microcuries with 0.5 microcuries being a suitable value. Levels of radioactivity higher than this level are operable, but are not considered desirable because of their higher cost.

Disposed on top of tray 1 is a cover member 4. Cover 4 is preferably made of transparent material such as glass, acrylic plastic, etc. Cover 4 is optionally provided with a series of recesses 5 which register with chambers 2 of tray 1. If desired, one end of the cover can be provided with a lip or other device to assure proper registration of the recesses with the chambers. The top of each recess 5 is coated with a thin layer of a scintillation compound designated by reference numeral 6.

Scintillation materials are well known in the art, and an appropriate scintillation compound could be selected by one skilled in the art. One suitable material is a mixture marketed commercially under the trademark LIQUIFLUOR by New England Nuclear, Boston, Massachussetts, comprising 100 grams of PPO (2, 5-diphenyloxazole) and 1.25 grams of POPOP (p-bis(2-(5-phenyloxazoyl)) benzene) in 1 liter of toluene. The scintillation material is applied to cover 4 by inverting the cover and disposing a sufficient amount of the solution in each recess 5 to wet the bottom surface of the recess. The toluene is then evaporated leaving an adherent coating of scintillation material. If desired, the evaporation process may be accelerated by directing a gentle stream of warm air against the wetted surface.

The scintillation compound layer is then covered with a carbon dioxide absorbent layer 7. Numerous carbon dioxide absorbing materials are known in the art, and it is within the skill of the art to select an appropriate absorber. Alkali metal hydroxides such as sodium hydroxide are particularly suitable.

The carbon dioxide absorbent layer may be applied by wetting the scintillation compound coated surface with a dilute aqueous solution of carbon dioxide absorber, such as 0.1 N sodium hydroxide, followed by evaporation of the aqueous solvent.

In addition to alkali, other carbon dioxide absorbing materials might be utilized. However, some common carbon dioxide absorbing materials such as Hyamine and its vapor are toxic to many biologically active species. If potentially toxic materials are utilized, they must not be allowed to contact the culture medium containing the biologically active species being characterized. Assuming separation of the culture medium and the carbon dioxide absorber can be maintained, the use of biologically toxic substances as carbon dioxide absorbers may be a useful way of sterilizing the carbon dioxide absorber and scintillation compound in order to prevent contamination of the test sample by extraneous organisms. If separation cannot be maintained, carbon dioxide absorbing substances which are toxic to microbial life should be avoided.

It will be readily recognized that numerous variations of the foregoing procedures are possible. For example, recesses 5 could be omitted from cover 4. The principal functions of recesses 5 are to confine the scintillation compound and carbon dioxide absorbing solutions during application of the scintillation compound and carbon dioxide absorbing coatings on the cover and also to provide a measure of protection for the coatings after application. Other possible modifications include application of the carbon dioxide absorbing layer prior to the application of scintillation compound layer, simultaneous application of the scintillation compound and carbon dioxide absorber in a common solution, application of a mixed powder of scintillation compound and carbon dioxide absorber in a thin coating of adhesive, etc. The essential thing is that the scintillation compound and carbon dioxide absorber be disposed adjacent the light-permeable wall section of the cell in intimate proximity to each other, out of contact with the $^{14}$C-labeled metabolizable substrates. Any effective means of achieving this is considered to be within the scope of the invention.

Initially, tray 1 and substrates 3a, 3b, 3c should be sterile. Tray 1 may be sterilized by thermal or chemical means such as by autoclaving or by treatment with gases. The microbiologically metabolizable substrates 3a, 3b, 3c may be sterilized together with tray 1, or if the sterilization procedure utilized for tray 1 is detrimental to the substrates, they may be sterilized separately and then deposited in the chambers 2 of tray 1 under aseptic conditions.

Disposed between tray 1 and cover 4 is a gasket 8 formed from soft rubber or rubber-like plastic. Gasket 8 serves to seal tray 1 to cover 4 so that when the cover is applied to the tray, the chambers 2 and recesses 5 form a series of air-tight cells. Alternatively, a grease sealant material could be interposed between the tray and the cover.

If desired, appropriate means may be provided to secure cover 4 to tray 1 such as spring clips 9.

Cover 4 with the scintillation compound and carbon dioxide absorber disposed in recesses 5 is preferably also sterilized, but under appropriate circumstances need not necessarily be sterile.

Figure 4:
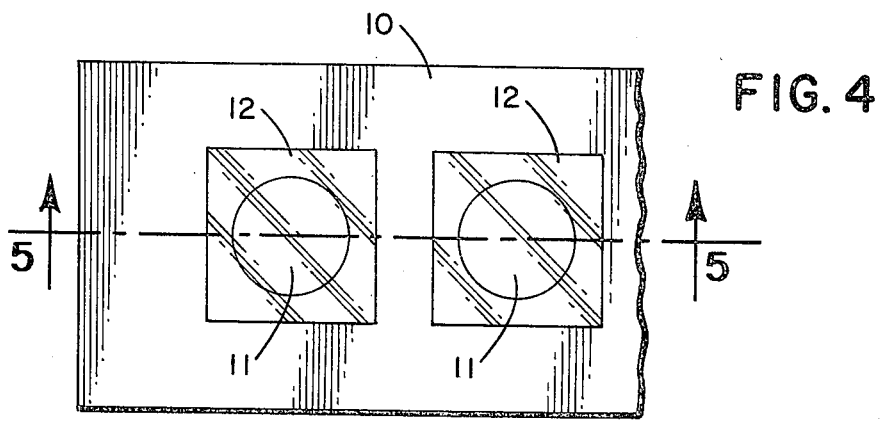
FIG. 4 is a plan view of a modified form of cover for the apparatus of the invention.
Figure 5:
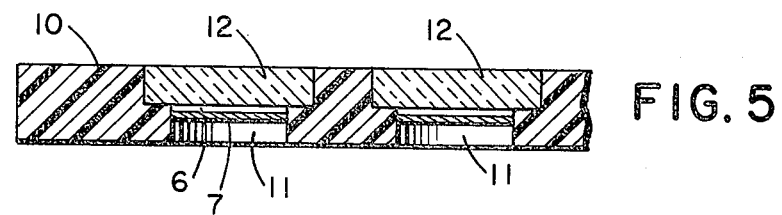
FIG. 5 is a sectional view taken along line 5—5 of FIG. 4.

FIGS. 4 and 5 show an alternate form of cover for the apparatus of the invention. Cover 10 comprises a sheet of material which may be rigid, opaque plastic of the same type utilized in the manufacture of tray 1. Cover 10 is provided with a series of apertures 11 adapted to register with chambers 2 when the cover is disposed on tray 1. Apertures 11 are closed off by pieces of transparent sheet material 12 such as glass, transparent acrylic plastic, or the like. Apertures 11 thus constitute recesses analogous to the recesses 5 on cover 4. A coating of scintillation compound and a coating of carbon dioxide absorber are applied to each transparent sheet 12 of cover 10 the same as on cover 4.

The embodiment of cover disclosed in FIG. 4 has the advantage that the sections of the cover between adjacent cells are opaque so that cross talk between adjacent cells is positively prevented.

Broadly stated, the method of the invention comprises providing a plurality of gas-tight cells having a light-permeable wall section and each containing different $^{14}$C-labeled substrates susceptible to biological activity, a carbon dioxide absorber and a scintillation compound in intimate proximity to each other adjacent the light-permeable wall section and remote from the $^{14}$C-labeled substrates, and an axenic sample of a biologically active agent; subjecting said cells for a period of time to conditions conducive to biological activity; and thereafter measuring the light emitted by the scintillation compound in each cell through the light-permeable wall section. The aforementioned cells may be provided by providing a plurality of sterile chambers, depositing a different $^{14}$C-labeled substrate susceptible to biological activity in each chamber, introducing an axenic sample of a biologically active agent into each chamber, and sealing the chambers with a gas-tight transparent cover having a carbon dioxide absorber and a scintillation compound coated on the inside thereof in intimate proximity to each other.

The method of the invention might be practiced utilizing a plurality of totally separate sample bottles which are light transparent or which are provided with transparent covers. However, it is most convenient when the test cells are all disposed on a single integral body as in the above-described apparatus. The use of cells disposed on a single integral body also eliminates a potential source of error which could arise from confusion of several different sample bottles.

The chambers may be sterilized either thermally or chemically with or without the $^{14}$C-labeled substrates therein. If it is desired to sterilize the chambers thermally and one or more of the substrates is sensitive to thermal degradation, then it is recommended that the chambers and the substrates be sterilized separately, and the substrates thereafter deposited in the chambers under aseptic conditions. If the $^{14}$-C-labeled substrates are all heat stable, then it is possible to deposit the substrates in un-sterile chambers, and thereafter to sterilize the chamber and the substrate simultaneously. Since chemical sterilization procedures may result in contamination of the $^{14}$C-labeled substrates, if it is desired to sterilize the chambers chemically, it is recommended that the sterilization of chamber and substrate be carried out separately.

It is essential that the sample of biologically active material which is to be characterized be axenic, i.e., that it consist of a single biologically active species free of contamination by other living organisms. In other words, it must be a pure culture sample. If a mixture of biologically active species is present in the test sample, then the result will indicate the combined activity of both species, and with no means to attribute what portion of the activity is due to which species, precise characterization of either species is not possible. Methods for isolating an axenic culture such as culturing smears, are known in the art and will not be described in detail herein.

One exception to the requirement for a totally axenic sample is in the case of viruses. Such viruses are inherently parasitic and require the existence of a viable host organism as a prerequisite for their own activity, isolation of a single host organism infected with a single virus is the closest practicable approximation to isolation of a pure culture.

The sample of biologically active material should be introduced along with a suitable culture medium, such as peptone broth, nutrient broth, or tryptic soy broth in order to assure that all essential nutrients for biological activity are present. If a proper culture medium is not supplied, then negative test results may result not from the absence of a particular biologically active species, but instead from the absence of an essential nutrient for that species. Typical nutrient media generally contain water, a carbon source, a nitrogen source, calcium, magnesium, potassium, phosphate, sulfate and trace amounts of other minor elements. The medium may also include a buffer for pH adjustment or maintenance. The carbon source may be glucose, sucrose, fructose, xylose, maltose, lactose, etc. or mixtures of the foregoing. However, it is usually desirable to use a minimally supportive medium, such as nutrient broth, lacking in carbohydrates and amino acids to force the growing organisms to use the $^{14}C$-labeled substrate if it can.

The nitrogen source may be nitrate, nitrite, ammonia, urea or any other assimilable organic or inorganic nitrogen source. Sufficient nitrogen should be present to facilitate cell growth.

A variety of calcium, potassium, and magnesium salts may be employed in the culture medium including the chlorides, sulfates, phosphates and the like. Similarly, phosphate and sulphate ions can be supplied as a variety of salts. As such materials are conventional in fermentation media, the selection of specific materials as well as their proportions is thought to be within the skill of the art.

The so-called minor elements which are present in trace amounts are commonly understood to include manganese, iron, zinc, cobalt, and possibly others.

Due to the fact that most biologically active species cannot function in strongly acidic or strongly alkaline media, suitable buffers such as potassium or ammonium phosphates may be employed to maintain the pH of the culture media near neutral, if desired.

It should be noted that the $^{14}C$ activity in the system initially resides in the substrate material deposited in each cell, and there should be no $^{14}C$ activity in the culture medium that is added with the sample of biologically active material.

The sealing of each chamber to form a gas-tight cell is effected for two reasons: (1) to prevent contamination of the test sample and (2) to prevent escape of radioactive $^{14}CO_2$. Ordinarily is to be preferred that the sealing means and cover be sterile, but under circumstances where contact between the culture medium and the cover does not occur so that contamination of the culture medium from the cover is unlikely, it may be possible to dispense with sterilization of the sealing means or cover.

The sealed cell must contain a carbon dioxide absorber and a scintillation compound in intimate proximity to each other. The purpose of the carbon dioxide absorber is to trap radioactive $^4CO_2$ which is released as a result of the metabolic action of a biologically active agent on a susceptible $^{14}C$-labeled substrate and to hold the radioactive $^{14}CO_2$ near the scintillation compound. The beta decay of the $^{14}CO_2$ causes the scintillation compound to emit flashes of light which signal the fact that the labeled substrate was susceptible to the action of the particular biologically active species undergoing the test. Each cell is provided with a transparent wall section and the carbon dioxide absorber and scintillation compound are disposed adjacent to such wall section in order to enable detection of the light flashes from outside the chamber without disruption of the ongoing biological activity. Conveniently this is achieved by utilizing a light-permeable cover with the carbon dioxide absorber and scintillation compound coated thereon as described hereinabove, however it is certainly possible to utilize chambers having transparent walls and to dispose the carbon dioxide absorber and scintillation compound next to the wall above the level of the culture medium on a piece of impregnated filter paper or some other way. All that is necessary is that the scintillation compound and the carbon dioxide absorber to be close enough to each other that radioactive $^{14}CO_2$ trapped by the carbon dioxide absorber has an appreciable effect on the scintillation compound; that the scintillation compound and carbon dioxide absorber be out of contact with the culture medium so that the scintillation compound is not appreciably affected by decay of the $^{14}C$-atoms in the un-metabolized substrate and that the scintillation compound and carbon dioxide absorber be sufficiently close to a light-permeable wall section of the cell to enable detection outside the cell of light flashes from the scintillation compound.

After the cells are sealed with the $^{14}C$-labeled substrate, the biologically active species, the culture medium, and the carbon dioxide absorber and scintillation compound inside, the cells are subjected to conditions conductive to biological activity. This is necessary in order for the biologically active species to grow and act upon susceptible $^{14}C$-labeled substrates, thereby releasing radioactive $^{14}CO_2$ into the atmosphere of the cell from which it is absorbed by the carbon dioxide absorber and held in suitable position to excite the scintillation compound. Factors which must be considered in establishing conditions conducive to biological activity are temperature, aeration, light, and acidity/alkalinity.

The activity of most medically significant bacteria is enhanced at temperatures in the range from about 35° to about 37° C. Consequently, a standard procedure would involve incubation at such a temperature. However, some organisms achieve optimum growth at a temperature of 20° C or lower while others may exhibit optimum growth at 45° C or higher. Thus, one skilled in the art would be required to employ any temperature best suited to the given circumstances.

Some biologically active species are destroyed by oxygen and thus are obligatory anerobes. Characterization of such species will require that free oxygen be excluded from the test cells. This may be achieved by assembling the cell in an oxygen free isolation box having, for example, a nitrogen atmosphere.

Some biologically active species are phototoxic, i.e. they are destroyed by light. Characterization of such species naturally would require the exclusion of light.

Finally, some biologically active species glow only in environments exhibiting a specific range of acidity or alkalinity. The use of suitable buffering agents in the culture medium is recommended as a procedure for maintaining conditions conducive to growth of such species.

Selection of suitable conditions is generally within the skill of the art. For example, a suitable standard procedure for medical laboratory testing would involve incubation in the presence of oxygen at approximately 37° C at a near neutral pH since growth of most medically significant bacteria is maximized under such conditions.

After a short delay following inoculation, the biologically active species in the sample will begin to grow rapidly in the medium. If the substrate in a particular cell is susceptible to the biological action of the particular species, the metabolic action of that species will generate $^{14}CO_2$ which in acid or nearly neutral media will pass out of the solution and diffuse into the cell atmosphere. The radioactive $^{14}CO_2$ gas is captured by the carbon dioxide absorber, and the decay of $^{14}C$ produces light flashes from the scintillation compound which is intimately associated therewith.

The rapidity with which a biologically active species will break down any given amount of susceptible $^{14}C$-labeled substrate depends on the number of organisms which are available to attack the substrate. Consequently, the greater the number of viable organisms present in the initial inoculum in each cell, the more rapidly the result of the metabolic activity of the biologically active species will reach detectable levels. On the other hand, excessively large numbers of microorganisms may rapidly exhaust the supply of an essential growth factor in the cell thereby inducing cessation of biological activity with consequent destruction of the usefulness of the characterization test. Accordingly, a balance must be maintained in selecting the size of the sample inoculum. An inoculum of from $10^5$ from about to about $10^8$ viable organisms is ordinarily appropriate.

Figure 6:
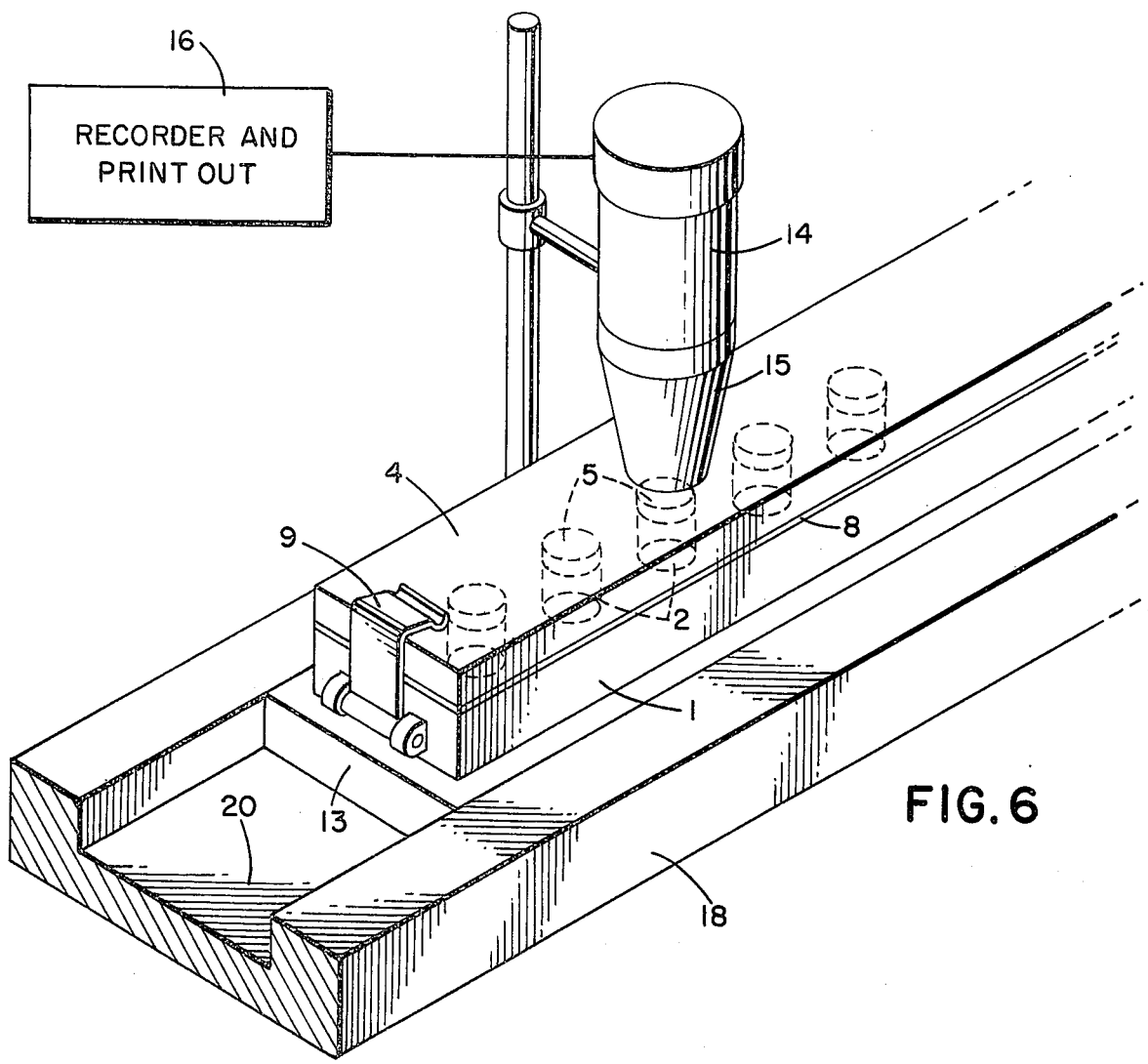
FIG. 6 is a perspective view of a preferred form of assaying apparatus according to the invention.

After a suitable incubation period which may be anywhere from about 15 minutes to 24 hours or more, but preferably is from about ½ to about 3 hours, the light emitted by the scintillation compound in each cell is measured. A preferred method of achieving this is to pass the cells seriatim past a photomultiplier which generates an electrical signal proportional to the number of flashes of light detected. A light guide may be interposed between the cells and the photomultiplier in order to prevent distortion of the test results by light from other sources. FIG. 6 shows one arrangement in which a tray of the type illustrated in FIGS. 1 through 5 is mounted on a carriage 13 which moves along a track 20 in table 18 beneath a photomultiplier 14 which is provided with a light guide 15. The sensitivity of such photomultipliers is sufficient that light flashes from the scintillation compound can be detected up to several inches away.

Carriage 13 is adapted for intermittent movement at predetermined time intervals so that the light generated by the scintillation compound in one cell has been measured for a given period of time, the tray will be advanced to move the next cell into position so that the light flashes generated by the scintillation compound in that cell can be measured.

The measurement period for each cell need not be long. For example, a period from about 30 to about 60 seconds is sufficient to provide a thoroughly accurate indication of the amount of radioactive $^{14}CO_2$ which has been generated in a cell. The electrical values generated by the photomultiplier in response to the light emitted from each cell may be recorded graphically or transformed into a printout of numerical values. FIG. 6 shows photomultiplier 14 schematically connected to a recorder 16.

If desired after the light from each cell has been measured, the tray may be returned to its original position with the first cell aligned with a photomultiplier and the measurement sequence may be repeated in order to chart the activity of the biologically active species over a period of time.

By comparing the activity pattern of a biologically active species with respect to a series of different $^{14}C$-labeled substrate materials, to known classification schemes or activity patterns, the method and apparatus may be utilized to identify a given species of bacteria. Possibly, the electrical signals could be transmitted directly to a computer programmed to analyze the pattern of data and generate a list of biologically active agents that fit the measured activity pattern. In some instances a given $^{14}C$-labeled substrate may be specific for a given species or at least for a known group, and in such cases a test of a single cell may be utilized to determine the presence or absence of such species or of members of such groups.

A procedure for characterizing a bacteria is as follows. Small amounts of sterile, $^{14}C$-labeled fermentable substrate materials are placed in separate chambers of a sterile, multi-chamber tray of the type illustrated in FIGS. 1 and 2. The substrates utilized are dextrin, fructose, galactose, glucose, lactose, maltose, mannitol and sucrose. The $^{14}C$-labeled substrates in each of the separate chambers are deposited in amounts sufficient to provide about .5 microcuries radioactivity.

An axenic culture of bacteria isolated from pus taken from an abscessed wound is sampled by picking up a small amount of the culture with a sterile wire, and the sample is suspended in about 1.5 ml. of dextrose free tryptic soy broth. After thorough mixing, a sterile pipette is used to place 0.1 ml. of the sample broth suspension in successive chambers at one minute intervals. A transparent cover of the type illustrated in FIGS. 1 and 2 with a scintillation compound and an alkali carbon dioxide absorber coated in recesses registering with the substrate containing chambers, is placed on the tray and secured. A gasket between the cover and the tray ensures that each chamber and recess form a sealed, gas-tight cell. The assemblage is then placed in an incubator for 90 minutes at 37° C. The bacteria in each cell grow, and in cells where the labeled substrate can be metabolized by the bacteria, radioactive $^{14}CO_2$ is produced. Any radioactive $^{14}CO_2$ produced in each cell is accumulated by the alkali carbon dioxide absorber and held in close proximity to the scintillation compound where decay of the $^{14}C$ atoms will cause the scintillation compound to emit flashes of light.

After incubation the assemblage is placed on the carriage of an assaying apparatus of the type illustrated in FIG. 6. The carriage is programmed to position the transparent cover of each cell successively in alignment with the light guide of a sensitive photomultiplier at one minute intervals in the same order in which samples were originally deposited in the respective chambers.

The photomultiplier measures the light emitted from each cell by the scintillation compound and produces an electric signal which can be quantified and recorded.

Values in excess of the emmissions generated by normal background radiation are characterized as positive (+); the remaining cells are noted as negative (−). The results are tabulated as follows:

| Substrate | Results |
|---|---|
| dextrin | − |
| fructose | + |
| galactose | + |
| glucose | + |
| lactose | − |
| maltose | + |
| mannitol | − |
| sucrose | + |

Reference to a standard microbiology identification manual such as *Bergey's Manual of Determinative Bacteriology*, 7th Ed., Williams & Wilkins, Baltimore, 1957, shows that the foregoing activity pattern is characteristic of the bacteria *Proteus vulgaris*.

Particular advantages of the method and apparatus of the invention lie in the miniaturization of the apparatus, the development of a simple, preformed assembly requiring little operator handling, the provision of a simple inexpensive apparatus which may be discarded after each test, minimization of laboratory technician contact with radioactive $^{14}C$ containing compounds, facilitation of automated testing, incubation and subsequent analysis taking place in the same chamber, and the ability to obtain very rapid test results.

The foregoing embodiments of the method and apparatus of the invention have been described solely for the purpose of illustrating and exemplifying the invention and not by way of limitation. Since modifications of the invention may occur to others skilled in the art, the scope of the invention is to be limited solely by the scope of the appended claims.

I claim:
1. Apparatus for characterization of a biologically active agent comprising:
    a. a plurality of sterile chambers containing different $^{14}C$-labeled fermentable substrates,
    b. means to facilitate introduction of an axenic sample of a biologically active agent to be characterized into each chamber,
    c. means for sealing each chamber to form a gas-tight cell having a light permeable wall section,
    d. a carbon dioxide absorber in each cell, and
    e. a scintillation compound in each cell in intimate proximity to said carbon dioxide absorber;
    said carbon dioxide absorber and said scintillation compound in each cell being disposed adjacent said light permeable wall section and out of contact with said $^{14}C$-labeled fermentable substrates.
2. Apparatus as recited in claim 1 further comprising means to measure light emitted by said scintillation compound through said light permeable wall section.
3. Apparatus as recited in claim 2 further comprising light guide means communicating between said transparent wall section and said measuring means.
4. Apparatus as recited in claim 2 wherein said measuring means comprises a photomultiplier.
5. Apparatus as recited in claim 2 further comprising means to move said measuring means successively into alignment with the transparent wall section of each cell.
6. Apparatus as recited in claim 2 further comprising means to record values measured by said measuring means.
7. A device as recited in claim 1 wherein said $^{14}C$-labeled fermentable substrates are selected from the class consisting of monosaccharides, disaccharides, polysaccharides, amino acids, salts of carboxylic acids, dicarboxylic acids and salts thereof, glycerol, polyhydroxy alcohols, hydroxy-carboxylic acids, and uracil.
8. Apparatus as recited in claim 1 wherein said chambers are sterilizable.
9. Apparatus as recited in claim 1 wherein said chambers are formed in a single integral body.
10. Apparatus as recited in claim 1 wherein said cavities are formed of opaque material and said sealing means comprises a transparent cover.
11. Apparatus as recited in claim 10 wherein said cover comprises a flat sheet of transparent material, and a gasket means interposed between said transparent sheet and said $^{14}C$-labeled substrate containing chambers.
12. Apparatus as recited in claim 11 wherein said transparent cover is glass.
13. Apparatus as recited in claim 11 wherein each chamber has an opening and said sheet of transparent material is provided with a recess aligned to register with the opening of each chamber.
14. Apparatus as recited in claim 13 wherein said cover is provided with optical absorption capacity between cells in order to prevent cross talk.
15. Apparatus as recited in claim 13 wherein said recesses are coated with a scintillation compound and a carbon dioxide absorber.
16. Apparatus as recited in claim 15 wherein said carbon dioxide absorber is sodium hydroxide.
17. Apparatus as recited in claim 1 wherein said carbon dioxide absorber comprises an alkali metal or alkaline earth metal hydroxide.
18. Apparatus as recited in claim 1 wherein said scintillation compound comprises a mixture of 2,5-diphenyloxazole and p-bis(2-(5-phenyloxazoyl)) benzene.
19. Apparatus as recited in claim 1 wherein said $^{14}C$-labeled substrates are coated on the chamber walls.
20. Apparatus as recited in claim 1 wherein said $^{14}C$-labeled substrates are solidified in agar.
21. Apparatus as recited in claim 1 wherein $^{14}C$-labeled substrates are absorbed on a sheet of paper.
22. Apparatus as recited in claim 1 further comprising means to subject said cells to conditions conducive to biological activity.
23. Apparatus as recited in claim 22 wherein said culture medium is selected from the class consisting of peptone broth, dextrose free tryptic soy broth, and nutrient broth.
24. Apparatus as recited in claim 1 further comprising a culture medium disposed in each chamber.
25. A method for characterization of a biologically active agent comprising the steps of:
    a. providing a plurality of sterile containers with different $^{14}C$-labeled fermentable substrates therein;
    b. introducing a sample of an axenic biologically active material to be characterized into each container;
    c. sealing said containers with a gas-tight transparent cover having a carbon dioxide absorber and a scin- tillation compound coated on the inside thereof in intimate proximity to each other;

d. subjecting the sealed containers to conditions conducive to biological activity for a predetermined period of time; and e. thereafter measuring the light emitted by said scintillation compound in each container through the transparent cover.

26. A method as recited in claim 25 wherein said containers are formed in a single integral body.

27. A method as recited in claim 25 wherein said cover comprises a sheet of transparent glass.

28. A method as recited in claim 25 wherein fermentable substrates are selected from the class consisting of monosaccharides, disaccharides and polysaccharides, amino acids, urea, uracil, carboxylic acids, dicarboxylic acids and salts thereof, hydroxycarboxylic acids, and polyhydroxy alcohols.

29. A method as recited in claim 25 wherein said fermentable substrates are coated on the walls of the chamber.

30. A method as recited in claim 25 wherein said fermentable substrates are solidified in agar.

31. A method as recited in claim 25 wherein said fermentable substrates are absorbed on a paper sheet.

32. A method as recited in claim 25 wherein said containers contain a culture medium.

33. A method as recited in claim 32 wherein said culture medium is selected from the class consisting of peptone broth, dextrose free tryptic soy broth, and nutrient broth.

34. A method as recited in claim 25 wherein said axenic sample of a biologically active agent comprises a viable inoculum of from about $10^5$ to about $10^8$ microorganisms suspended in a culture medium.

35. A method as recited in claim 25 wherein said conditions conducive to biological activity comprise incubation in the presence of oxygen at a temperature lying in the range from about 35° to about 37° C at a pH between 6 and 8 for a time interval lying in the range from about 15 minutes to about 3 hours.

36. A method as recited in claim 35 wherein said predetermined incubation is carried out for a time interval lying in the range from about 1 hour to about 2 hours.

37. A method as recited in claim 25 wherein said emitted light is measured by means of a photomultiplier.

38. A method as recited in claim 37 wherein said photomultiplier is successively aligned with the transparent cover of each chamber.

39. A method as recited in claim 25 wherein said carbon dioxide absorber comprises an alkali metal or an alkaline earth metal hydroxide.

40. A method as recited in claim 39 wherein said carbon dioxide absorber comprises sodium hydroxide.

41. A method as recited in claim 25 wherein said scintillation compound comprises 2-, 5-diphenyloxazole.

42. A method as recited in claim 25 further comprising the step of recording the measured valves for the light emitted by the scintillation compound in each chamber.

43. A method for characterization of a biologically active agent as recited in claim 25 wherein said biologically active material is an unknown agent, and further comprising the step of comparing the activity pattern of said biologically active material to known activity data in order to identify the unknown agent.

44. A method for characterization of a biologically active agent comprising the steps of:

a. providing a plurality of gas-tight cells each having light-permeable wall section and containing:
 1. different $^{14}C$-labeled fermentable substrates,
 2. a carbon dioxide absorber and a scintillation compound disposed in intimate proximity to each other adjacent said light-permeable wall section and out of contact with said $^{14}C$-labeled fermentable substrates, and
 3. an axenic sample of material to be tested for biological activity, b. subjecting said chambers to conditions conductive to biological activity for a predetermined period of time; and c. thereafter measuring the light emitted by said scintillation compound in each chamber through said light permeable wall section.

45. A method for characterization of a biologically active agent as recited in claim 44 wherein said biologically active material is an unknown agent, and further comprising the step of comparing the activity pattern of said biologically active material to known activity data in order to identify the unknown agent.

46. A method for characterization of biologically active agent comprising the steps of:

a. providing a plurality of sterile containers with different culture media each containing a $^{14}C$-labeled fermentable substance therein;

b. introducing a sample of an axenic biologically active material to be characterized into each container;

c. sealing said containers with a gas-tight light permeable cover having a carbon dioxide absorber and a scintillation compound coated on the inside thereof in intimate proximity to each other;

d. subjecting the sealed containers to conditions conducive to biological activity for a predetermined period to time; and e. thereafter measuring the light emitted by said scintillation compound in each container through the light permeable cover.

47. A method for characterization of a biologically active agent as recited in claim 46 wherein said biologically active material is an unknown agent, and further comprising the step of comparing the activity pattern of said biologically active material to known activity data in order to identify the unknown agent.

* * * * *